United States Patent
Engelbart et al.

(10) Patent No.: US 8,934,702 B2
(45) Date of Patent: Jan. 13, 2015

(54) SYSTEM AND METHOD FOR DETERMINING CUMULATIVE TOW GAP WIDTH

(75) Inventors: Roger W. Engelbart, St. Louis, MO (US); Reed Hannebaum, Belleville, IL (US); Eric Rector, St. Charles, MO (US); Jeffrey Haywood, Belleville, IL (US)

(73) Assignee: The Boeing Company, Chicago, IL (US)

( * ) Notice: Subject to any disclaimer, the term of this patent is extended or adjusted under 35 U.S.C. 154(b) by 1673 days.

(21) Appl. No.: 11/968,395

(22) Filed: Jan. 2, 2008

(65) Prior Publication Data

US 2009/0169056 A1 Jul. 2, 2009
US 2012/0328159 A9 Dec. 27, 2012

Related U.S. Application Data

(60) Continuation-in-part of application No. 11/832,853, filed on Aug. 2, 2007, now Pat. No. 7,769,224, which is a division of application No. 10/726,099, filed on Dec. 2, 2003, now Pat. No. 7,289,656.

(51) Int. Cl.
*G06K 9/00* (2006.01)
*G01N 21/00* (2006.01)
*G01N 21/892* (2006.01)
(Continued)

(52) U.S. Cl.
CPC .............. *G01N 21/892* (2013.01); *B29C 70/38* (2013.01); *B64F 5/00* (2013.01); *G01B 11/022* (2013.01); *G01B 11/046* (2013.01); *G01N 21/8901* (2013.01); *G01N 2021/8472* (2013.01)
USPC ......... 382/141; 382/106; 382/149; 356/237.1

(58) Field of Classification Search
USPC ................... 382/141, 149, 192, 106; 156/64; 356/237.1, 237.3–237.4, 238.3
See application file for complete search history.

(56) References Cited

U.S. PATENT DOCUMENTS 3,879,245 A 4/1975 Fetherston et al.
4,064,534 A 12/1977 Chen et al.
(Continued)

FOREIGN PATENT DOCUMENTS

EP 0319797 A2 6/1989
EP 0833146 A2 4/1998
(Continued)

OTHER PUBLICATIONS

"British Aerospace Aircraft BAe 146," Flight International, May 2, 1981, 2 pages.
(Continued)

*Primary Examiner* — Sheela Chawan
(74) *Attorney, Agent, or Firm* — Yee & Associates, P.C.

(57) ABSTRACT

A system for determining cumulative tow gap width includes an in-process vision system having at least one camera adapted to record images of a composite material and a data analysis computer communicating with and adapted to receive image data from the in-process vision system. The data analysis computer may be adapted to calculate a cumulative gap width of tow gaps in the composite material. A user interface may communicate with and be adapted to receive data analysis results from the data analysis computer. A method for determining cumulative tow width gap of tow gaps in a composite structure is also disclosed.

20 Claims, 5 Drawing Sheets

(51) Int. Cl.

| | |
|---|---|
| B29C 70/38 | (2006.01) |
| B64F 5/00 | (2006.01) |
| G01B 11/02 | (2006.01) |
| G01B 11/04 | (2006.01) |
| G01N 21/89 | (2006.01) |
| G01N 21/84 | (2006.01) |

(56) References Cited

U.S. PATENT DOCUMENTS

| | | |
|---|---|---|
| 4,223,346 A | 9/1980 | Neiheisel et al. |
| 4,310,132 A | 1/1982 | Robinson et al. |
| 4,507,564 A | 3/1985 | Shimada |
| 4,548,859 A | 10/1985 | Kline et al. |
| 4,573,183 A | 2/1986 | Relihan |
| 4,608,220 A | 8/1986 | Caldwell et al. |
| 4,693,678 A | 9/1987 | Von Volkli |
| 4,699,683 A | 10/1987 | McCowin |
| 4,760,444 A | 7/1988 | Nielson et al. |
| 4,780,262 A | 10/1988 | Von Volkli |
| 4,790,898 A | 12/1988 | Woods |
| 4,830,298 A | 5/1989 | Van Blunk |
| 4,877,471 A | 10/1989 | McCowin et al. |
| 4,941,182 A | 7/1990 | Patel |
| 4,973,838 A | 11/1990 | Bell et al. |
| 4,986,189 A | 1/1991 | Theurer et al. |
| 5,024,399 A | 6/1991 | Barquet et al. |
| 5,058,497 A | 10/1991 | Bishop et al. |
| 5,153,668 A | 10/1992 | Katzir et al. |
| 5,198,983 A | 3/1993 | Blake et al. |
| 5,337,647 A | 8/1994 | Roberts et al. |
| 5,401,115 A | 3/1995 | Musil et al. |
| 5,412,302 A | 5/1995 | Kido et al. |
| 5,439,549 A | 8/1995 | Fryc et al. |
| 5,450,147 A | 9/1995 | Dorsey-Palmateer |
| 5,518,208 A | 5/1996 | Roseburg |
| 5,540,126 A | 7/1996 | Piramoon |
| 5,562,788 A | 10/1996 | Kitson et al. |
| 5,651,600 A | 7/1997 | Dorsey-Palmateer |
| 5,683,646 A | 11/1997 | Reiling, Jr. |
| 5,689,340 A | 11/1997 | Young |
| 5,700,337 A | 12/1997 | Jacobs et al. |
| 5,746,553 A | 5/1998 | Engwall |
| 5,804,276 A | 9/1998 | Jacobs et al. |
| 5,814,386 A | 9/1998 | Vasiliev et al. |
| 5,822,055 A | 10/1998 | Tsai et al. |
| 5,825,495 A | 10/1998 | Huber |
| 5,866,820 A | 2/1999 | Camplin et al. |
| 5,871,117 A | 2/1999 | Protasov et al. |
| 5,917,588 A | 6/1999 | Addiego |
| 5,949,901 A | 9/1999 | Nichani et al. |
| 5,963,660 A | 10/1999 | Koontz et al. |
| 5,979,531 A | 11/1999 | Barr et al. |
| 6,012,883 A | 1/2000 | Engwall et al. |
| 6,013,341 A | 1/2000 | Medvedev et al. |
| 6,045,651 A | 4/2000 | Kline et al. |
| 6,064,429 A | 5/2000 | Belk et al. |
| 6,074,716 A | 6/2000 | Tsotsis |
| 6,075,883 A | 6/2000 | Stern et al. |
| 6,086,696 A | 7/2000 | Gallagher |
| 6,106,649 A | 8/2000 | Slyne |
| 6,112,792 A | 9/2000 | Barr et al. |
| 6,168,358 B1 | 1/2001 | Engwall et al. |
| 6,184,924 B1 | 2/2001 | Schneider et al. |
| 6,205,239 B1 | 3/2001 | Lin et al. |
| 6,277,230 B1 | 8/2001 | Milko |
| 6,364,250 B1 | 4/2002 | Brinck et al. |
| 6,369,492 B1 | 4/2002 | Sugimoto |
| 6,390,169 B1 | 5/2002 | Johnson |
| 6,451,152 B1 | 9/2002 | Holmes et al. |
| 6,480,271 B1 | 11/2002 | Cloud et al. |
| 6,547,769 B2 | 4/2003 | Van Tassel et al. |
| 6,569,513 B2 | 5/2003 | Yamaji et al. |
| 6,639,662 B2 | 10/2003 | Vaez-Iravani et al. |
| 6,648,273 B2 | 11/2003 | Anast |
| 6,692,681 B1 | 2/2004 | Lunde |
| 6,725,123 B1 | 4/2004 | Denuell |
| 6,799,619 B2 | 10/2004 | Holmes et al. |
| 6,814,822 B2 | 11/2004 | Holmes et al. |
| 6,871,684 B2 | 3/2005 | Engelbart et al. |
| 6,937,753 B1 | 8/2005 | O'Dell et al. |
| 7,039,348 B2 | 5/2006 | Kerxhalli et al. |
| 7,039,485 B2 | 5/2006 | Engelbart et al. |
| 7,048,024 B2 | 5/2006 | Clark et al. |
| 7,080,441 B2 | 7/2006 | Braun |
| 7,083,698 B2 | 8/2006 | Engwall et al. |
| 7,134,629 B2 | 11/2006 | Johnson et al. |
| 7,137,182 B2 | 11/2006 | Nelson |
| 7,159,822 B2 | 1/2007 | Grantham et al. |
| 7,171,033 B2 | 1/2007 | Engelbart et al. |
| 7,190,459 B2 | 3/2007 | Reinhorn |
| 7,193,696 B2 | 3/2007 | Engelbart et al. |
| 7,197,177 B2 | 3/2007 | Lowe |
| 7,228,611 B2 | 6/2007 | Anderson et al. |
| 7,236,625 B2 | 6/2007 | Engelbart et al. |
| 7,282,107 B2 | 10/2007 | Johnson et al. |
| 7,289,656 B2 * | 10/2007 | Engelbart et al. ............. 382/141 |
| 7,325,771 B2 | 2/2008 | Stulc et al. |
| 7,350,379 B2 | 4/2008 | Ueda et al. |
| 7,362,437 B2 | 4/2008 | Engelbart et al. |
| 7,372,556 B2 | 5/2008 | Engelbart et al. |
| 7,385,567 B2 | 6/2008 | Lee |
| 7,424,902 B2 | 9/2008 | Engelbart et al. |
| 7,435,947 B2 | 10/2008 | Engelbart et al. |
| 7,489,392 B2 | 2/2009 | Engelbart et al. |
| 7,513,964 B2 | 4/2009 | Ritter et al. |
| 7,527,222 B2 | 5/2009 | Biornstad et al. |
| 7,716,835 B2 | 5/2010 | Johnson et al. |
| 7,769,224 B2 | 8/2010 | Engelbart et al. |
| 7,807,002 B2 | 10/2010 | Engelbart et al. |
| 7,835,567 B2 | 11/2010 | Oldani |
| 7,889,907 B2 | 2/2011 | Engelbart et al. |
| 7,978,328 B2 | 7/2011 | Engelbart et al. |
| 7,983,469 B2 | 7/2011 | Engelbart et al. |
| 8,050,486 B2 | 11/2011 | Walton |
| 8,068,659 B2 | 11/2011 | Engelbart et al. |
| 8,157,212 B2 | 4/2012 | Biornstad et al. |
| 8,182,628 B2 | 5/2012 | Biornstad et al. |
| 8,184,281 B2 | 5/2012 | Engelbart et al. |
| 2001/0002149 A1 | 5/2001 | Vaez-Iravani et al. |
| 2002/0141632 A1 | 10/2002 | Engelbart et al. |
| 2002/0168504 A1 | 11/2002 | Yamaji et al. |
| 2002/0176617 A1 | 11/2002 | Simonetti |
| 2003/0230178 A1 | 12/2003 | Steadman |
| 2004/0114025 A1 | 6/2004 | Kerxhalli et al. |
| 2004/0194506 A1 | 10/2004 | Ueda et al. |
| 2005/0025350 A1 | 2/2005 | Engelbart et al. |
| 2005/0047643 A1 | 3/2005 | Lowe |
| 2005/0117793 A1 | 6/2005 | Engelbart et al. |
| 2005/0203657 A1 | 9/2005 | Engelbart et al. |
| 2006/0108048 A1 | 5/2006 | Engelbart et al. |
| 2006/0109454 A1 | 5/2006 | Engelbart et al. |
| 2006/0152712 A1 | 7/2006 | Engelbart et al. |
| 2006/0191622 A1 | 8/2006 | Ritter et al. |
| 2007/0034313 A1 | 2/2007 | Engelbart et al. |
| 2007/0096019 A1 | 5/2007 | Engelbart et al. |
| 2007/0097359 A1 | 5/2007 | Engelbart et al. |
| 2007/0173966 A1 | 7/2007 | Oldani |
| 2007/0229805 A1 | 10/2007 | Engelbart et al. |
| 2007/0271064 A1 | 11/2007 | Walton |
| 2007/0280501 A1 | 12/2007 | Walton |
| 2008/0006102 A1 | 1/2008 | Engelbart et al. |
| 2008/0008380 A1 | 1/2008 | Engelbart et al. |
| 2008/0246175 A1 | 10/2008 | Biornstad et al. |
| 2009/0148030 A1 | 6/2009 | Engelbart et al. |
| 2010/0303335 A1 | 12/2010 | Engelbart et al. |
| 2011/0073708 A1 | 3/2011 | Biornstad et al. |

FOREIGN PATENT DOCUMENTS

| | | |
|---|---|---|
| EP | 0903574 A2 | 3/1999 |
| EP | 1030172 A2 | 8/2000 |
| EP | 1083076 A2 | 3/2001 |
| EP | 1503206 A1 | 2/2005 |

(56) References Cited

FOREIGN PATENT DOCUMENTS

| EP | 08 25 4166 | | 2/2009 |
|---|---|---|---|
| EP | 2056095 | A1 | 5/2009 |
| EP | 2077447 | A1 | 7/2009 |
| JP | 2001012930 | A | 1/2001 |
| WO | 9418643 | A1 | 8/1994 |
| WO | 2004025385 | A1 | 3/2004 |
| WO | 2005057497 | A1 | 6/2005 |
| WO | 2006001859 | A1 | 1/2006 |
| WO | 2006001860 | A2 | 1/2006 |
| WO | 2007078408 | A2 | 7/2007 |

OTHER PUBLICATIONS

"A Barrelful of Experience," Intervia, May 1992, 2 pages.
"Beechcraft's Composite Challenge," http://www.aerotalk.com/Beech/cfm, accessed Mar. 1, 2004, 2 pages.
Bruckstein et al., "Omniview Cameras with Curved Surface Mirrors," IEEE Omnidirectional Vision Proceedings, Jun. 12, 2000, 7 pages.
Engelbart et al., U.S. Appl. No. 10/628,691, filed Jul. 28, 2003, 34 pages.
Evans, "Fiber Placement," In: ASM Handbook vol. 21, Composites, Miracle et al. (Eds.), ASM International, Material Park, OH, pp. 477-479, 2001.
Fiedler et al., "Tango Composite Fuselage Platform," SAMPE Journal, vol. 39, No. 1, pp. 57-63, Jan./Feb. 2003.
Grimshaw et al. "Advanced Technology Tape Laying for Affordable Manufacturing of Large Composite Structures," Proceedings of the 46th International SAMPE Symposium and Exhibition, Long Beach, CA, May 6-10, 2001, 11 pages.
Grimshaw, "Automated Tape Laying," in: ASM Handbook vol. 21, Composites, Miracle et al. (Eds.), ASM International, Material Park, OH, pp. 480-485, 2001.
European Search Report dated Dec. 1, 2004, regarding Application No. EP 04076900 (EP 1503206), 3 pages.
International Search Report dated May 25, 2005, regarding Application No. PCT/US2004/039905 (WO 2005057497), 3 pages.
European Search Report dated Feb. 13, 2009, regarding Application No. EP 08253449 (EP 2056095), 3 pages.
Krupka et al., "Industrial Applications of Shearography for Inspection of Aircraft Components," Proceedings of the 8th European Conference of Nondestructive Testing, Barcelona, Jun. 17-21, 2002, 4 pages.
"Premier I Features Lighter, Stronger All-Composite Fuselage," http://www.cinmach.com/WolfTracks4_1/MTG_WT7.htm, 1998, 3 pages.
"Raytheon Aircraft Orders Four More Cincinnati Fiber Placement Systems for Industry's First Composite-Fuselage Business Jets," http://www.cinmach.com/compnews/PressReleases/pr00-11.htm, Jul. 20, 2000.
"Raytheon Aircraft's Hawker Horizon Reaches Fuselage Milestone," Raytheon Company News Release dated Oct. 9, 2000, 2 pages.
"Raytheon's New Quiet Jets," http://www.cts.com/king/vasci/newsletter/vol42.html, Mar. 2000, 2 pages.
Rocky Mountain Composites, Inc., "Filament Winding," http://www.rockymountaincomposites.com/wind_sys.htm, accessed Apr. 1, 2004, 1 page.
Scott, "Toyota-made Plane Makes Flight Debut," http://www.aviationnow.com/avnow/news/channel_busav.jsp?view=story&id=news/btoyo0607.xml, Jun. 7, 2002, 1 page.
Sharp et al., "Material Selection/Fabrication Issues for Thermoplastic Fiber Placement," Journal of Thermoplastic Composite Materials, vol. 8, Jan. 1995, 13 pages.
Zhang, "Lecture: Applied Sensor Technology," http://tech-www.informatik.uni-hamburg.de/lehre/ws2003/vorlesngen/angewandte_sensorik/vorlesung_03_pdf, Nov. 11, 2003, 40 pages.
USPTO Notice of Allowance dated Jun. 18, 2007 regarding U.S. Appl. No. 10/726,099, 26 pages.
USPTO Office Action dated Dec. 10, 2008 regarding U.S. Appl. No. 11/832,831, 11 pages.
USPTO Office Action dated Apr. 15, 2009 regarding U.S. Appl. No. 11/832,831, 18 pages.
USPTO Final Office Action dated Sep. 17, 2009 regarding U.S. Appl. No. 11/832,831, 16 pages.
USPTO Office Action dated Dec. 28, 2009 regarding U.S. Appl. No. 11/832,831, 14 pages.
USPTO Final Office Action dated May 3, 2010 regarding U.S. Appl. No. 11/832,831, 12 pages.
USPTO Office Action dated Sep. 15, 2010 regarding U.S. Appl. No. 11/832,831, 15 pages.
USPTO Notice of Allowance dated Mar. 17, 2011 regarding U.S. Appl. No. 11/832,831, 8 pages.
USPTO Office Action dated Jun. 10, 2009 regarding U.S. Appl. No. 11/832,853, 19 pages.
USPTO Final Office Action dated Nov. 18, 2009 regarding U.S. Appl. No. 11/832,853, 12 pages.
USPTO Notice of Allowance dated Mar. 22, 2010 regarding U.S. Appl. No. 11/832,853, 7 pages.
USPTO Office Action dated Feb. 22, 2011 regarding U.S. Appl. No. 11/927,115, 16 pages.
USPTO Notice of Allowance dated Jul. 20, 2011 regarding U.S. Appl. No. 11/927,115, 9 pages.
USPTO Office Action dated Feb. 4, 2011 regarding U.S. Appl. No. 12/813,329, 8 pages.
USPTO Notice of Allowance dated Jun. 29, 2011 regarding U.S. Appl. No. 12/813,329, 26 pages.
USPTO Notice of Allowance dated Jan. 24, 2012 regarding U.S. Appl. No. 12/813,329, 24 pages.

* cited by examiner

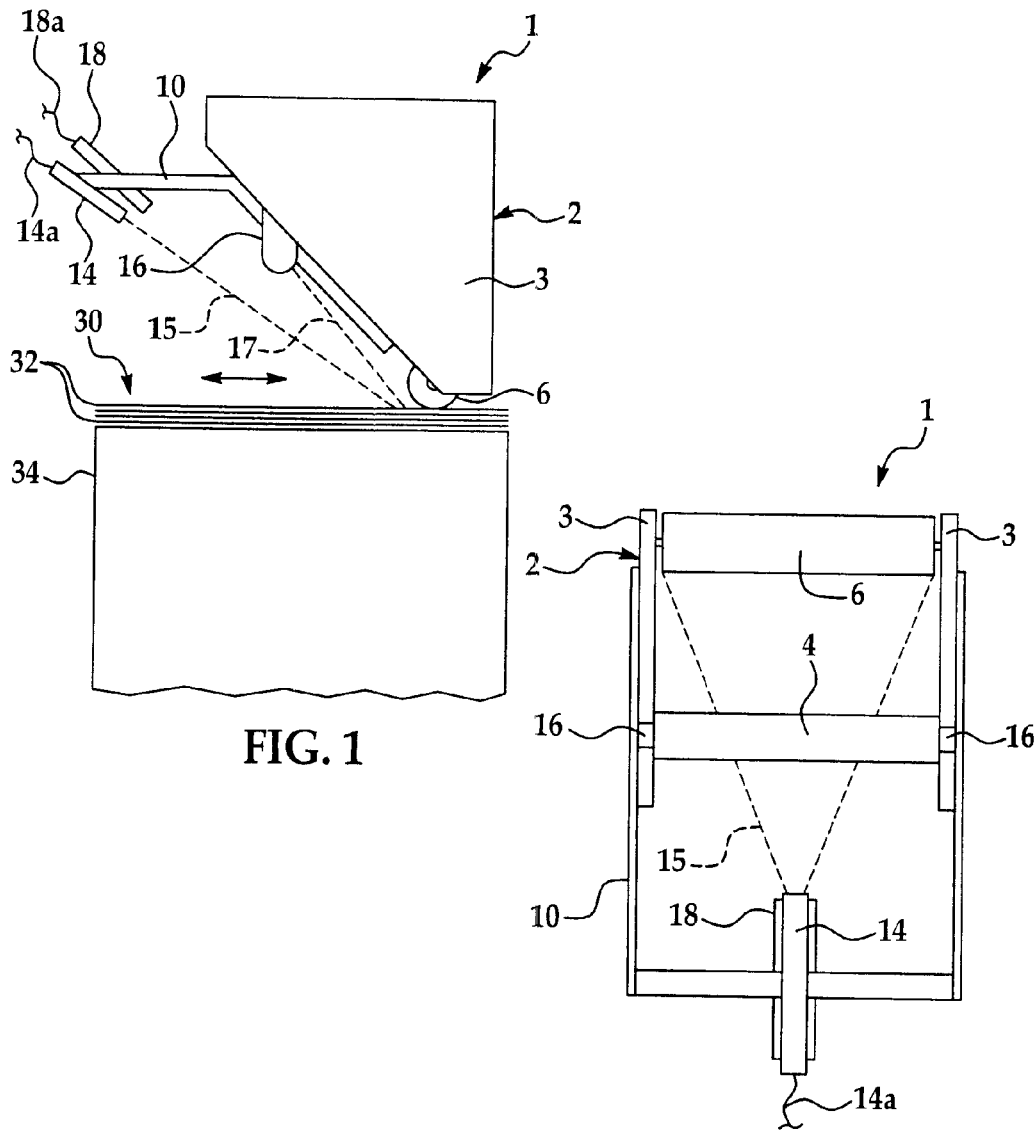
FIG. 1
FIG. 2
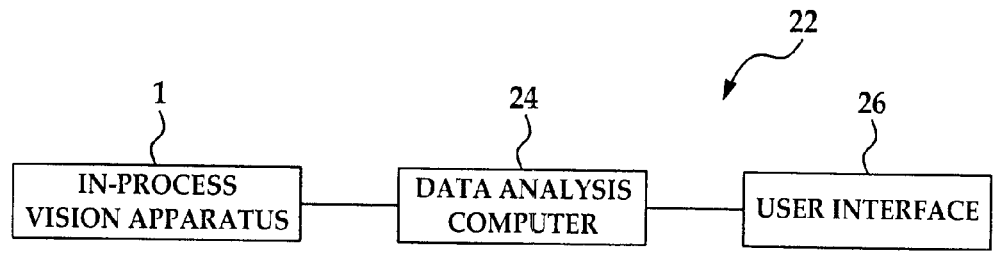
FIG. 3

SYSTEM AND METHOD FOR DETERMINING CUMULATIVE TOW GAP WIDTH

CROSS REFERENCE TO RELATED APPLICATIONS

The present application is a continuation-in-part of U.S. patent application Ser. No. 11/832,853, filed Aug. 2, 2007, now U.S. Pat. No. 7,769,224, issued Aug. 3, 2010, which is a divisional of U.S. patent application No. 10/726,099, filed Dec. 2, 2003, now U.S. Pat. No. 7,289,656, issued Oct. 30, 2007.

TECHNICAL FIELD

The disclosure relates to fabrication of composite structures. More particularly, the disclosure relates to a system and method for determining cumulative tow gap width in fabricated composite structures.

BACKGROUND

Methods of fabricating composite structures include the fiber placement or automated collation process. In such a process, one or more ribbons of composite material or tows may be laid down on a substrate which may be a tool, mandrel or one or more underlying and compacted layers of composite material. Conventional fiber placement processes may utilize a heat source to assist in compaction of the plies of composite material at a localized nip point. The ribbon or tow of composite material and the underlying substrate may be heated at the nip point to increase the tack of the resin of the plies while being subjected to compressive forces to ensure adhesion to the substrate. To complete the part, additional strips of composite material may be applied in a side-by-side manner to form layers and may be subjected to localized heat and pressure during the consolidation process.

A complex and detailed inspection guideline may be necessary for the inspection of composite structures that are fabricated using the fiber and tape placement processes. The guideline may establish acceptance criteria for discrete inconsistencies such as tow gaps, tow overlaps, twists, dropped tows and foreign objects. In-process vision technology may be capable of detecting and making accept/reject decisions on these inconsistencies during the manufacturing process. The guideline may also establish a requirement for maximum allowable cumulative, or total, tow gap width within any 12-inch area perpendicular to the direction of material placement or lay-down.

The existing solution to meeting the requirements of the inspection guidelines may include manual visual inspection by the human eye. An operator may select at random a number of regions of the correct size according to the inspection guideline. The operator may then apply a manual template that will define the area in which the inspection is to be made. The operator may utilize a means, of determining and documenting the location, of the region with respect to the entire surface area of the ply. Within each area, the operator may be required to visually identify tow gaps and measure each one manually using a tool such as a six-inch scale or a dial caliper. The widths of all identified gaps may be documented, the sum of the gap widths may be calculated and the sum for the specific area may be determined. The approach may be carried out on each ply of each part which is manufactured.

The existing solution to meeting the requirements of the inspection guidelines may require extensive cycle time and touch labor and may carry a high risk of inaccurate measurement. This approach may be viable for small parts but unmanageable for large surface areas. The approach may also be labor-intensive and prone to a high probability of error in measurement. Reduction of fatigue and risk of error may require multiple inspectors which may increase the touch labor required to complete the inspection.

The disclosure is generally directed to a system for determining cumulative tow gap width. An illustrative embodiment of the system includes an in-process vision system having at least one camera adapted to record images of a composite material and a data analysis computer communicating with and adapted to receive image data from the in-process vision system. The data analysis computer may be adapted to calculate a cumulative gap width of tow gaps in the composite material. A user interface may communicate with and be adapted to receive data analysis results from the data analysis computer.

The disclosure is further generally directed to a method for determining cumulative tow gap width of tow gaps in a composite structure. An illustrative embodiment of the method includes providing a composite material, recording periodic images of the composite material, analyzing the images of the composite material for presence of rejectable indications in the composite material and formulating a pass/fail status of the composite material based on the rejectable indications.

BRIEF DESCRIPTION OF THE ILLUSTRATIONS

FIG. 1 is a partially schematic side view of an in-process vision system of an illustrative embodiment of the system for determining cumulative tow gap width.

FIG. 2 is a top view of the in-process vision system shown in FIG. 1.

FIG. 3 is a block diagram of an illustrative embodiment of the system for determining cumulative tow gap width.

DETAILED DESCRIPTION

Figure 4:
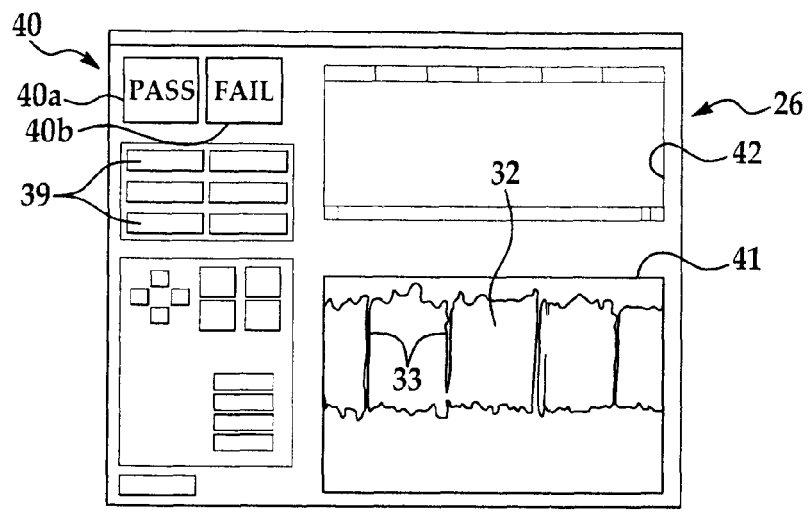
FIG. 4 is a screenshot of a vision system user interface.

The disclosure is generally directed to a system and method for determining tow gap width within any designated area of any ply or tow on the surface of a part or structure produced by automated material placement. The system and method may utilize archived in-process vision data for any automatically placed tow, query selected surface area regions on the tow and sum the detected tow gap widths within each surface area region of the tow. Accordingly, the system and method may extensively reduce inspection cycle times and enhance accuracy of tow gap width measurements in fabrication of composite materials.

Referring to the drawings, an illustrative embodiment of the system for determining cumulative tow gap width, hereinafter system, is generally indicated by reference numeral 22 in the schematic block diagram of FIG. 3. The system 22 may include an in-process vision apparatus 1 which is shown in FIGS. 1 and 2 and will be hereinafter described. The in-process vision apparatus 1 may be adapted to illuminate and view composite tape strips or tows 32 (FIG. 1), including tow gaps 33 (FIG. 5) which form in the tows 32 during consolidation of a composite structure 30 (FIG. 3). The in-process vision apparatus 1 may operate in conjunction with an automated fiber or material placement machine (not shown) which is known to those skilled in the art.

As shown in FIG. 3, a data analysis computer 24, having a user interface 26, may communicate with the in-process vision apparatus 1. The data analysis computer 24 may be adapted to receive and store images of selected queried surface regions on the tows 32 which are viewed by the in-process vision apparatus 1. Based on these images, the data analysis computer 24 may also be adapted to detect and calculate the cumulative gap width of the tow gaps 33 within the queried surface region or regions of the tows 32 (such as a 12-inch area, for example and without limitation) which may be perpendicular to the direction of material placement or lay-down of the tows 32. The data analysis computer 24 may further be adapted to compare the calculated cumulative tow gap width to maximum allowable cumulative tow gap width criteria. The data analysis computer 24 may be programmed to accept (pass) the tows 32 for continued fabrication of the composite structure 30 in the event that the calculated cumulative tow gap width meets the maximum allowable cumulative tow gap width criteria and reject (fail) the tows 32 for fabrication in the event that the calculated cumulative tow gap width does not meet the maximum allowable cumulative tow gap width criteria.

A screenshot of a suitable exemplary user interface 26 for the data analysis computer 24 is shown in FIG. 4. The user interface 26 may include, for example and without limitation, various control inputs 39; a pass/fail indicator 40; an inspection window 41 which presents a real-time image frame of the region on the tow or tows 32 which is being viewed by the in-process vision apparatus 1; and a defects window 42. The control inputs 39 of the user interface 26 may facilitate the entering and changing of parameters such as acceptance (pass/fail) criteria and image frame size of the image presented in the inspection window 41, for example and without limitation. In the example shown in FIG. 4, a sample of a tow 32 with tow gaps 33 of several different widths is shown in the inspection window 41. The defects window 42 of the of the user interface may indicate the breadth, angle, length and/or other parameters of the tow gaps 33 in the tows 32.

The pass/fail indicator 40 of the user interface 26 may include a pass button 40a and a fail button 40b. The data analysis computer 24 may be adapted to illuminate the pass button 40a in the event that the calculated cumulative tow gap width meets the maximum allowable cumulative tow gap width criteria and may be adapted to illuminate the fail button 40b in the event that the calculated cumulative tow gap width does not meet the maximum allowable cumulative tow gap width criteria. The pass button 40a may be a highly-visible color such as red and the fail button 40b may be a different color such as green, for example and without limitation.

An exemplary structure for the in-process vision apparatus 1 is shown in FIGS. 1 and 2. Generally, the in-process vision apparatus 1 may include a frame 2 which may include a pair of spaced-apart frame plates 3, as shown in FIG. 2. Each of the frame plates 3 may have a generally triangular shape, as shown in FIG. 1. At least one frame plate connector 4 (FIG. 2) may extend between the frame plates 3. A compaction roller 6 may extend between the frame plates 3.

A laser mount bracket 10 may extend from the frame plates 3 of the frame 2. At least one laser 14 having laser wiring 14a may be provided on the laser mount bracket 10. The laser 14 may be adapted to emit a laser beam 15 generally toward the compaction roller 6. At least one digital camera 18 having camera wiring 18a may also be provided on the laser mount bracket 10. At least one area light 16 may be provided on the laser mount bracket 10, or on one or both of the frame plates 3 of the frame 2, generally between the camera 18 and the compaction roller 6. As shown in FIG. 2, in some embodiments, an area light 16 may be provided on each frame plate 3 of the frame 2. Each area light 16 may be adapted to emit a light beam 17 (FIG. 1) generally toward the compaction roller 6.

As further shown in FIG. 1, in typical application of the system 22, the in-process vision apparatus 1 may be positioned over a composite structure 30 which may include multiple adjacent strips or tows 32 of composite tape. The in-process vision apparatus 1 may be supported over the composite structure 30 using any suitable support structure (not shown). The tows 32 may include multiple fibers embedded in a resin or other material which becomes tacky or flowable upon the application of heat. The tows 32 may be arranged on a work surface 34 such as a table or mandrel, for example and without limitation, and may be compacted to form the composite structure 30 according to an automated collation technique which is known to those skilled in the art. For example, an article entitled "Material Selection/Fabrication Issues for Thermoplastic Fiber Placement" by Richard Sharp et al. published in the "Journal of Thermoplastic Composite Materials" (January 1995) discusses one conventional fiber placement process and is incorporated herein by reference.

Figure 6:
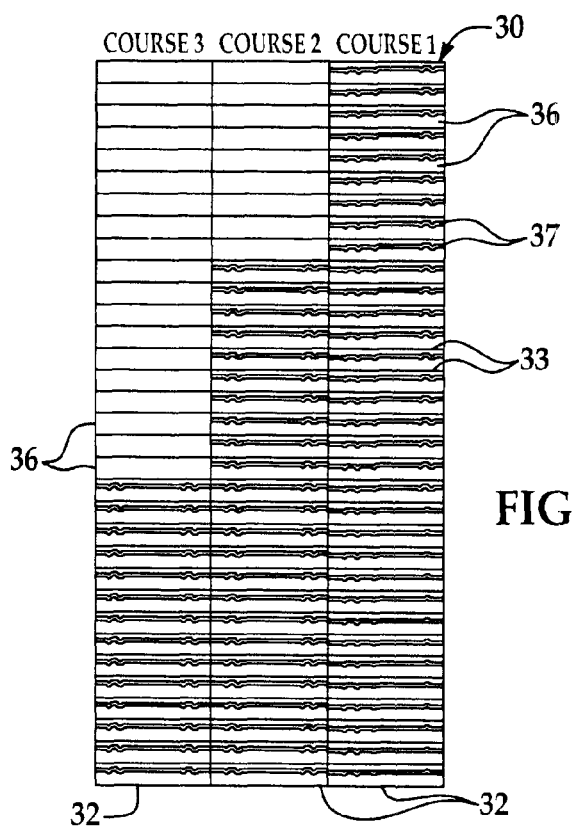
FIG. 6 is a simulated multi-course laminate utilized for laboratory validation.

The automated collation process may include guiding the tows 32 from material creels (not shown) to the automated collation or fiber placement machine (not shown) with which the in-process vision apparatus 1 works in conjunction. In particular, the tows 32 may be sequentially and automatically guided onto the work surface 34 beneath the in-process vision apparatus 1 and fed under the compaction roller 6. Focused heat energy may then be applied to the incoming tow 32 and the underlying previously-compacted tows 32 that were previously laid on the work surface 34. With the combination of heat and pressure applied by the compaction roller 6, the tow 32 is consolidated into the previous layer of compacted tows 32, thus forming an additional layer of the composite structure 30. As shown in FIG. 6, multiple tows 32 may be laid side-by-side on the work surface 34 to form multiple adjacent courses of the composite structure 30. During the consolidation process, the compaction roller 6 may be moved along the tows 32 as indicated by the double-headed arrow in FIG. 1.

Figure 5:
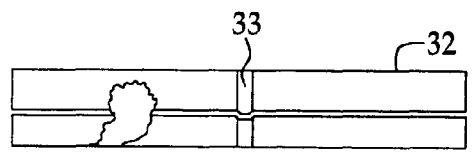
FIG. 5 is a sectional view of a pair of laminated composite tape strips, with a tow gap in the tape strips.

During compaction of the tows 32 into the composite structure 30, inconsistencies such as the tow gaps 33 shown in FIG. 5 may form between laminated tows 32. Therefore, the system 22 may be operated to view and record surface regions on the composite structure 30, and the tow gaps 33 which have formed in the tows 32 in each surface region, during consolidation for the purpose of calculating a cumulative tow gap width of the tow gaps 33. By comparing the calculated cumulative tow gap width of the tow gaps 33 to maximum allowable cumulative tow gap width criteria for the tow gaps 33, the data analysis computer 24 of the system 22 may determine whether to accept (pass) or reject (fail) the tows 32 for fabrication of the composite structure 30. Accordingly, the laser 14 (FIGS. 1 and 2) of the in-process vision apparatus 1 may be operated to emit the laser beam 15 against the surface of the tows 32 at a selected surface region which is generally adjacent or proximate to the compaction roller 6. The area light or lights 16 may also be operated to emit the light beam or beams 17 against the surface of the tows 32 to illuminate the region. The camera 18 may be operated to view the illuminated region on the surface of the tows 32.

The images which are sighted by the camera 18 of the in-process vision apparatus 1 may be transmitted to and stored in the memory of the data analysis computer 24 (FIG. 3) of the system 22. At that point, the data analysis computer 24 may calculate the cumulative tow gap width of the tow gaps 33 in the tows 32 corresponding to the selected surface area on the composite structure 30 and compare the calculated cumulative tow gap width to maximum allowable. Cumulative tow gap width criteria which may have been previously pre-stored in the memory of the data analysis computer 24. In the event that the calculated cumulative tow gap width meets the maximum allowable cumulative tow gap width criteria, the data analysis computer 24 of the system 22 may accept or pass the tows 32 for further fabrication of the composite structure 30. In that case, the data analysis computer 24 may illuminate the pass button 40a of the pass/fail indicator 40 on the user interface 26 shown in FIG. 4. On the other hand, in the event that the calculated cumulative tow gap width does not meet the maximum allowable cumulative tow gap width criteria, the data analysis computer 24 may reject the tows 32 for further fabrication of the composite structure 30. In that case, the data analysis computer 24 may illuminate the fail button 40b of the pass/fail indicator 40 on the user interface 26.

The data analysis computer 24 may display each image frame which is sighted by the camera 18 in real time in the inspection window 41 (FIG. 4) of the user interface 26. The size of the image frame may be selectively adjusted by operation of the control inputs 39 (FIG. 4) of the user interface 26.

FIG. 6 illustrates multiple image frames 36 of a simulated multi-course laminate utilized for laboratory validation. The laminate or composite structure 30 includes three courses of the tows 32 labeled "Course 1", "Course 2" and "Course 3", respectively, from right to left. The multiple individual image frames 36 which are viewed sequentially by the camera 18 of the in-process vision apparatus 1 (FIGS. 1-3) throughout the course of consolidation are shown on each tow 32. A laser line 37 which is formed by impingement of the laser beam (FIG. 1) of the laser 14 on the surface of the tows 32 is shown in each image frame 36. Each laser line 37 is distorted to reveal a tow gap 33 between stacked or laminated tows 32 in each course. Since the composite structure 30 may include multiple side-by-side courses of the tows 32, as in FIG. 6, each image frame 36 of the camera 18 may cover more than one course in some applications.

Figure 7:
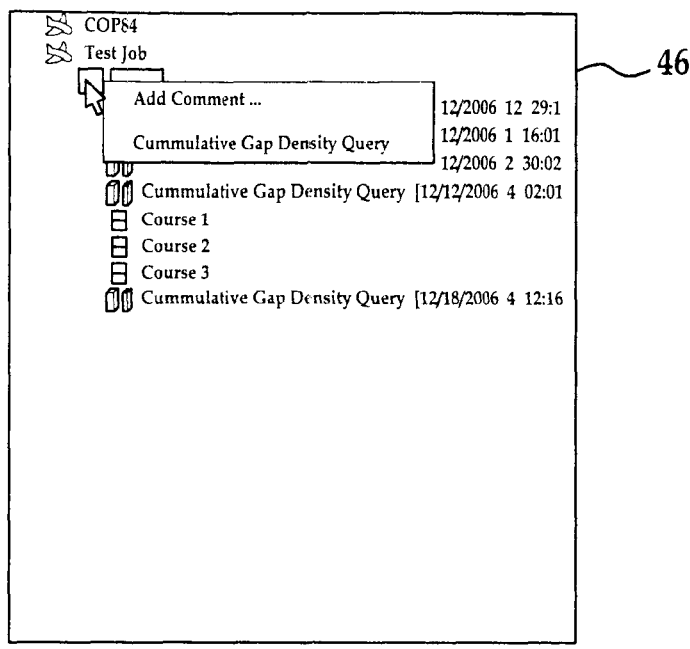
FIG. 7 illustrates a menu for selection of a cumulative gap query.

The image frames 36 on the multiple courses of tows 32 shown in FIG. 6 may be displayed on the data analysis computer 24 by, for example, calling up the menu 46 shown in FIG. 7 and selecting "Test Job" and clicking on "Ply 1" on the menu 46. The process of determining the cumulative gap width of the tow gaps 33 may then be initiated by right-clicking on "Ply 1" and selecting "Cumulative Gap Density Query" on the menu 46. The menu 46 may be designed to include a complete list of parts or composite structures 30; under each may be available the cumulative gap determination result by ply number.

Figure 8:
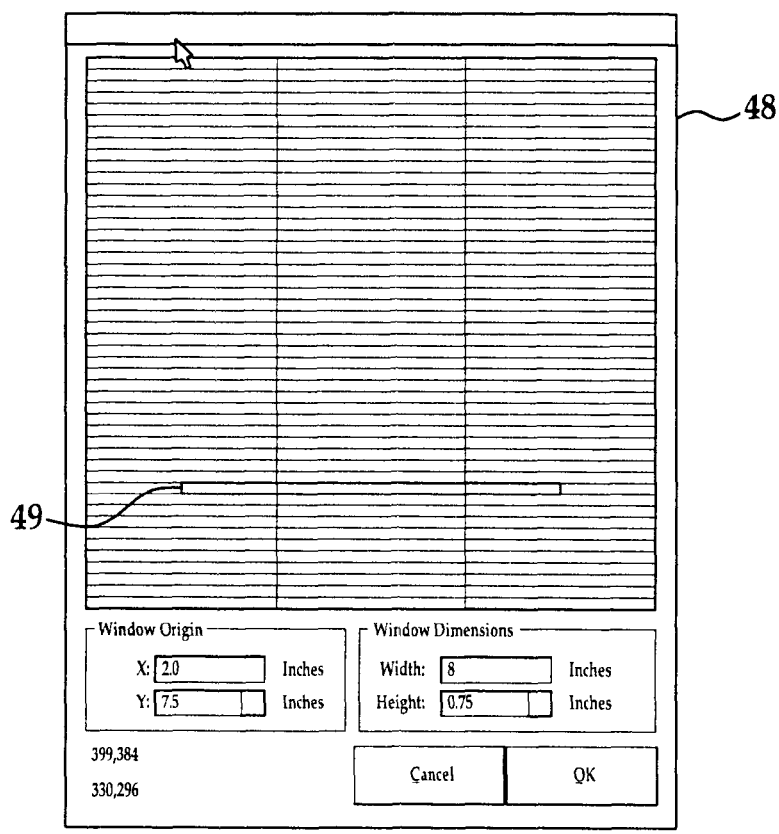
FIG. 8 is a front view of a selection of cumulative gap query interface.

The cumulative gap density query interface 48 shown in FIG. 8 may facilitate selection of the dimensions of the query window or immediate region within which the cumulative gap is being calculated. In the cumulative gap density query interface 48, the length of the query window 49 corresponds to the width of two of the three material courses. The query window 49 may be any selected dimensions; as it is "stepped" sequentially across the ply, the gaps are totaled within each region covered.

Figure 9:
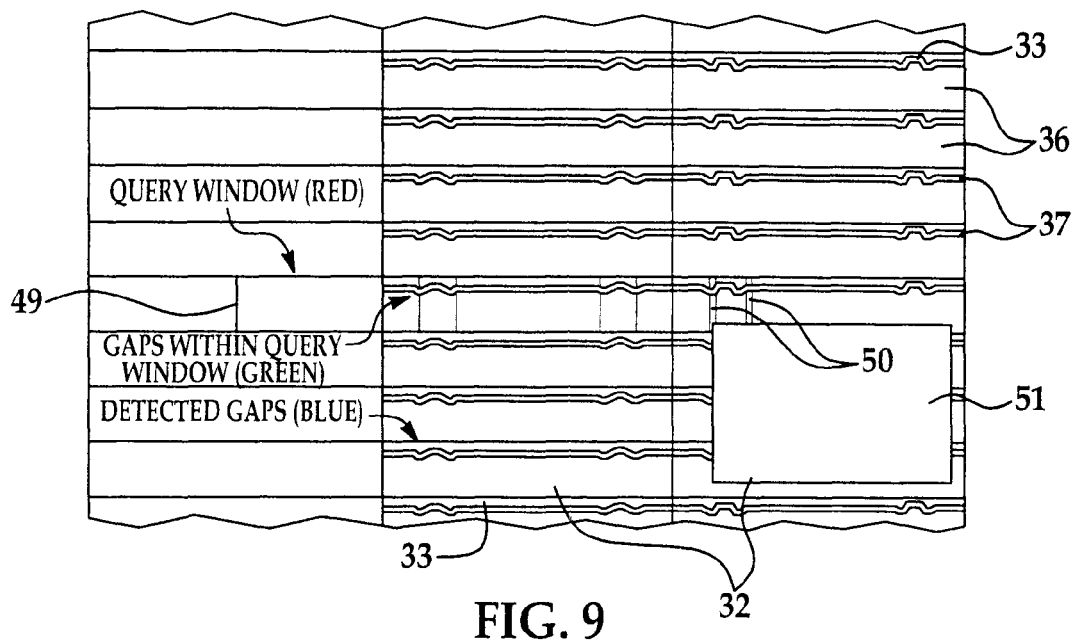
FIG. 9 is a window which illustrates cumulative gap analysis.

When the size of the query window 49 has been selected, clicking "OK" on the cumulative gap density query interface 48 may generate an image such as the one shown in FIG. 9. Tow gaps 33 are indicated in the solid lines on the image. Highlighting a particular tow gap 33 may provide the ply course and image frame in which the gap was detected; it may also provide the width of the tow gap 33 and its x coordinate location. Gap indicator lines 50 in the query window 49 may indicate the gaps that are being totaled inside the query window 49. Positioning of the cursor in the query window 49 may display the result of the query in a query result box 51. The total cumulative gap width may be the sum of the gaps found inside the query window 49. In the example shown in FIG. 9, the height of the query window 49 equals the height of one image frame 36. The cumulative gap width density may be the total cumulative gap width divided by the query window 49 area.

Figure 10:
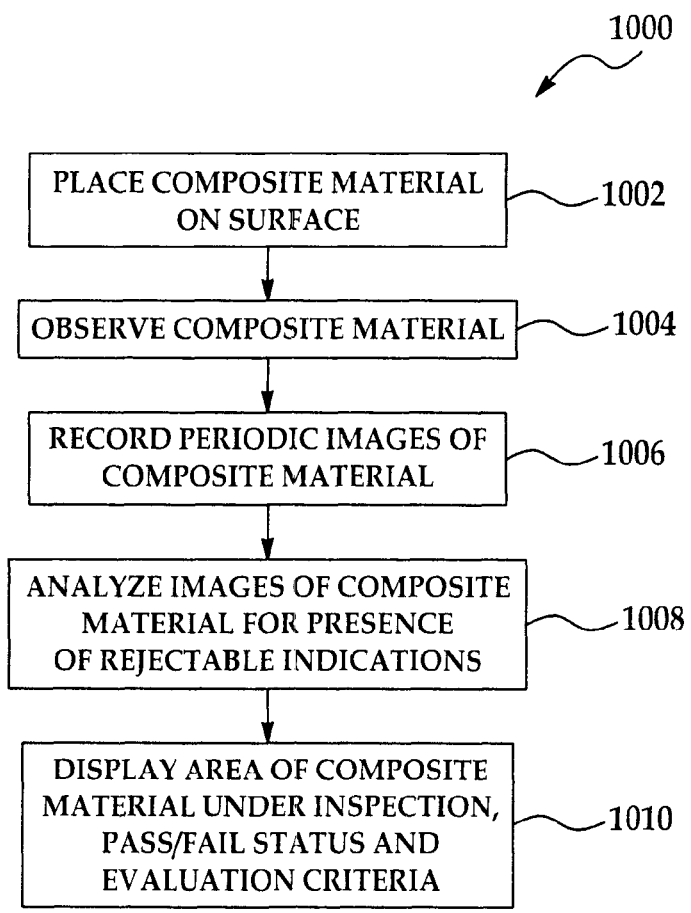
FIG. 10 is a flow diagram of an illustrative method for determining cumulative tow gap width.

Referring next to FIG. 10, a flow diagram 1000 of an illustrative method for determining cumulative tow gap width is shown. In block 1002, composite material may be placed on a surface. In block 1004, the composite material may be observed. In block 1006, periodic images of the composite material may be recorded. In block 1008, images of the composite material may be analyzed for the presence of rejectable indications. In block 1010, the area; the pass/fail status; and evaluation criteria of the composite material under inspection may be displayed.

Figure 11:
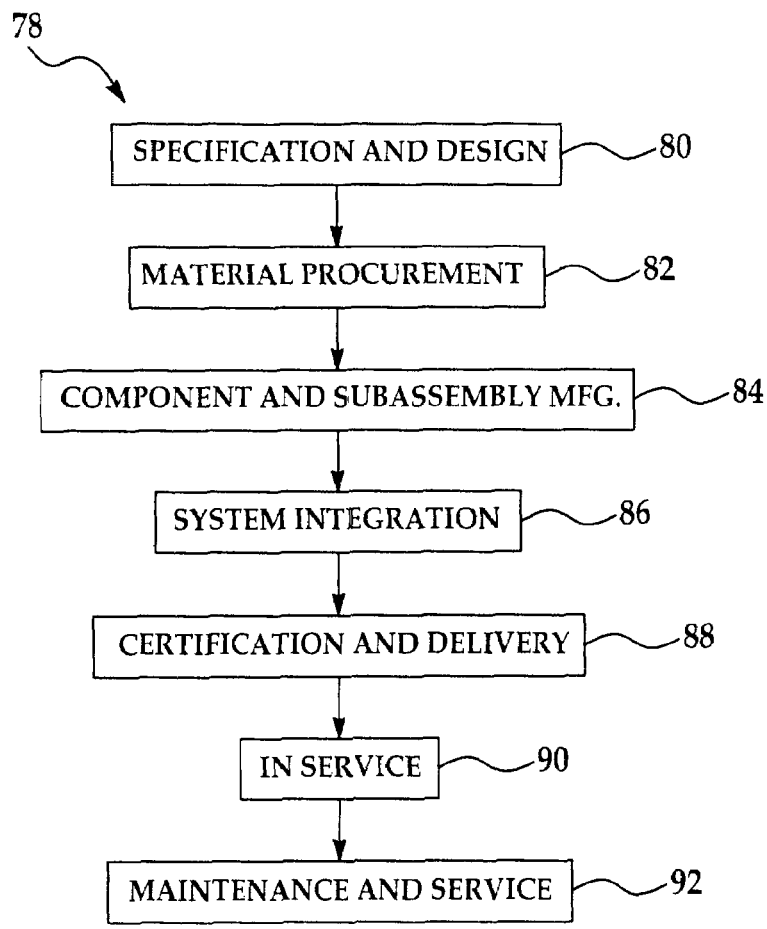
FIG. 11 is a flow diagram of an aircraft production and service methodology.
Figure 12:
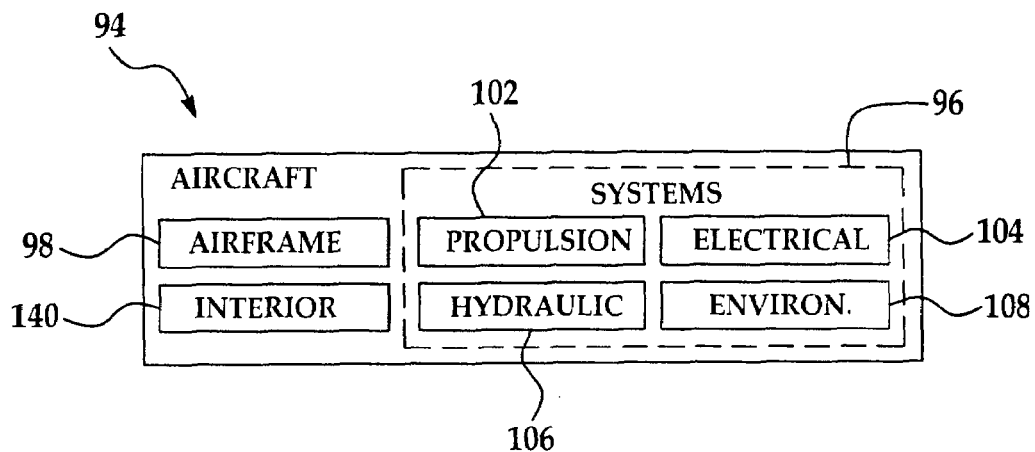
FIG. 12 is a block diagram of an aircraft.

Referring next to FIGS. 11 and 12, embodiments of the disclosure may be used in the context of an aircraft manufacturing and service method 78 as shown in FIG. 11 and an aircraft 94 as shown in FIG. 12. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 12, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A system for determining cumulative tow gap width, comprising:
    an in-process vision system having at least one camera adapted to record images of a composite material;
    a data analysis computer communicating with and adapted to receive image data from said in-process vision system;
    said data analysis computer is adapted to calculate a cumulative gap width of tow gaps in the composite material; and
    a user interface communicating with and adapted to receive data analysis results from said data analysis computer.

2. The system of claim 1 wherein said in-process vision system comprises a frame and at least one laser carried by said frame.

3. The system of claim 2 further comprising at least one area light carried by said frame.

4. The system of claim 1 wherein said data analysis computer is adapted to compare said cumulative gap width of tow gaps in the composite material to maximum allowable cumulative tow gap width criteria.

5. The system of claim 4 wherein said data analysis computer is adapted to indicate a pass status of the composite material when said cumulative gap width of tow gaps in the composite material meets said maximum allowable cumulative tow gap width criteria.

6. The system of claim 5 wherein said data analysis computer is adapted to indicate a fail status of the composite material when said cumulative gap width of tow gaps in the composite material does not meet said maximum allowable cumulative tow gap width criteria.

7. The system of claim 6 wherein said user interface comprises a pass/fail indicator having a pass button and a fail button and said data analysis computer is adapted to illuminate said pass button when said data analysis computer indicates said pass status and said data analysis computer is adapted to illuminate said fail button when said data analysis computer indicates said fail status.

8. The system of claim 1 wherein said data analysis computer is adapted to display said image data.

9. A system for determining cumulative tow gap width, comprising:
    an in-process vision system and at least one camera adapted to record images of a composite material;
    a data analysis computer communicating with and adapted to receive and store image data from said in-process vision system;
    said data analysis computer is adapted to query selected regions on the composite material and calculate a cumulative gap width of tow gaps in the selected regions; and
    a user interface communicating with and adapted to receive data analysis results from said data analysis computer.

10. The system of claim 9 wherein said in-process vision system comprises a frame and at least one laser carried by said frame.

11. The system of claim 10 further comprising at least one area light carried by said frame.

12. The system of claim 9 wherein said data analysis computer is adapted to compare said cumulative gap width of tow gaps in the composite material to maximum allowable cumulative tow gap width criteria.

13. The system of claim 12 wherein said data analysis computer is adapted to indicate a pass status of the composite material when said cumulative gap, width of tow gaps in the composite material meets said maximum allowable cumulative tow gap width criteria.

14. The system of claim 13 wherein said data analysis computer is adapted to indicate a fail status of the composite material when said cumulative gap width of tow gaps in the composite material does not meet said maximum allowable cumulative tow gap width criteria.

15. The system of claim 14 wherein said user interface comprises a pass/fail indicator having a pass button and a fail button and said data analysis computer is adapted to illuminate said pass button when said data analysis computer indicates said pass status and said data analysis computer is adapted to illuminate said fail button when said data analysis computer indicates said fail status.

16. The system Of claim 9 wherein said data analysis computer is adapted to display said image data.

17. A method for determining cumulative tow width gap of tow gaps in a composite structure, comprising:
    providing a composite material;
    recording periodic images of said composite material;
    analyzing said images of said composite material for presence of rejectable indications in said composite material; and
    formulating a pass/fail status of said composite material based on said rejectable indications, said steps of recording, analyzing, and formulating comprising a computer executing programmed instructions stored in computer readable media.

18. The method of claim 17 wherein said analyzing said images of said composite material for presence of rejectable indications in said composite material comprises analyzing said images of said composite material for cumulative width of tow gaps in said composite material.

19. The method of claim 18 wherein said formulating a pass/fail status of said composite material based on said rejectable indications comprises:
    establishing a maximum allowable-cumulative tow gap width criteria,
    comparing said cumulative width of tow gaps in said composite material with said maximum allowable cumulative tow gap width criteria,
    passing said composite material when said cumulative width of tow gaps in said composite material meets said maximum allowable cumulative tow gap width criteria, and
    failing said composite material when said cumulative width of tow gaps in said composite material does not meet said maximum allowable cumulative tow gap with criteria.

20. The method of claim 17 further comprising displaying said periodic images of said composite material.

* * * * *